United States Patent [19]

Reynolds

[11] Patent Number: 5,554,125
[45] Date of Patent: Sep. 10, 1996

[54] PREFILLED VIAL SYRINGE

[76] Inventor: David L. Reynolds, 305 Knowlton Road, P.O. Box 600, (Knowlton) Lac Brome, Quebec, Canada, J0E 1V0

[21] Appl. No.: 245,132

[22] Filed: May 17, 1994

Related U.S. Application Data

[63] Continuation-in-part of Ser. No. 791,399, Nov. 16, 1991, Pat. No. 5,364,369, which is a continuation-in-part of Ser. No. 437,203, Nov. 16, 1989, Pat. No. 5,137,527, which is a continuation-in-part of Ser. No. 72,015, Jul. 8, 1987, Pat. No. 4,886,495.

[30] Foreign Application Priority Data

Nov. 14, 1990 [GB] United Kingdom .................. 9024710
May 17, 1993 [GB] United Kingdom .................. 9310084

[51] Int. Cl.⁶ .................................................. A61M 5/00
[52] U.S. Cl. .......................... 604/187; 604/200; 604/201; 604/203
[58] Field of Search ....................... 604/82, 87, 88, 604/89, 91, 92, 191, 187, 200, 201, 203, 204, 205, 411, 413, 414, 415, 416, 905, 232, 218, 220

[56] References Cited

U.S. PATENT DOCUMENTS

| | | | |
|---|---|---|---|
| 3,074,541 | 1/1963 | Roehr | 604/201 |
| 3,091,240 | 5/1963 | McConnaughey et al. | 604/218 |
| 3,699,961 | 10/1972 | Szpur | 604/89 |
| 3,811,441 | 5/1974 | Sarnoff | 604/218 |
| 3,967,759 | 7/1976 | Baldwin et al. | 604/218 |
| 3,976,069 | 8/1976 | Ong | 604/218 |
| 4,031,890 | 6/1977 | Homan | 604/218 |
| 4,820,272 | 4/1989 | Palmer | 604/218 |
| 4,850,966 | 7/1989 | Grau et al. | 604/82 |
| 4,861,335 | 8/1989 | Reynolds | 604/191 |
| 4,886,495 | 12/1989 | Reynolds | 604/191 |
| 5,106,372 | 4/1992 | Ranford | 604/220 |
| 5,137,511 | 8/1992 | Reynolds | 604/191 |
| 5,281,198 | 1/1994 | Haber et al. | 604/218 |
| 5,334,162 | 8/1994 | Harris | 604/88 |
| 5,352,036 | 10/1994 | Haber et al. | 604/82 |
| 5,354,284 | 10/1994 | Haber et al. | 604/232 |
| 5,364,369 | 11/1994 | Reynolds | 604/191 |
| 5,374,249 | 12/1994 | Haber et al. | 604/82 |

Primary Examiner—Corrine M. Maglione
Assistant Examiner—N. Kent Gring

[57] ABSTRACT

A prefilled syringe for one or two component medicaments is based upon the use of a vial containing a medicament or one component of a medicament, the vial having an open bottom closed by a piston. When a flexible extension of the piston is coupled with a tubular plunger, and an adaptor cap having an internal needle and an external connection for a needle is placed over a cap of the vial, the latter is converted into a prefilled syringe. The open bottom of the vial is configured so as not to interfere with handling of the vials by conventional vial sterilizing, filling and capping machinery, and may be formed so as to provide an internal shoulder which will secure a piston retention member.

14 Claims, 9 Drawing Sheets

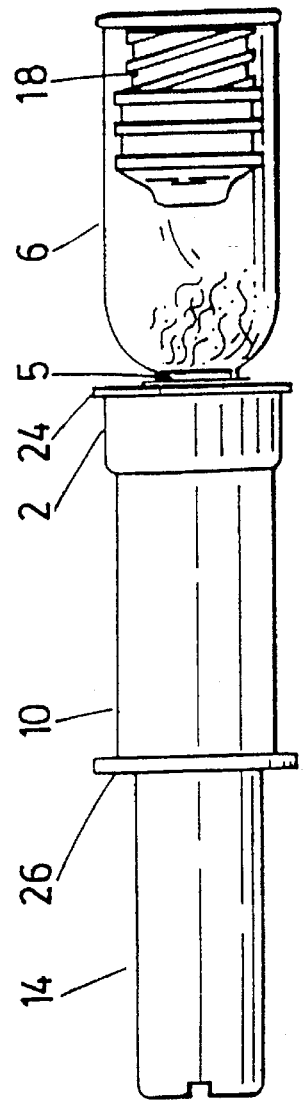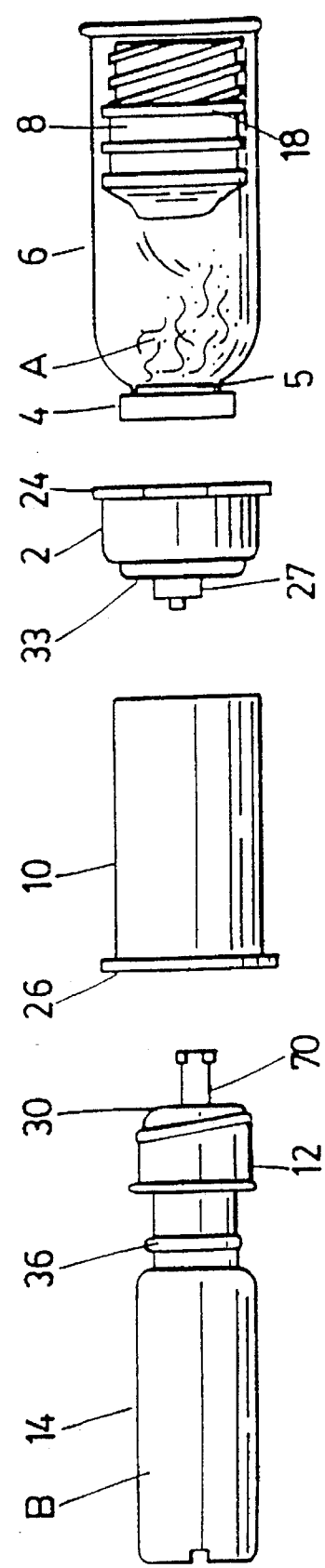

PREFILLED VIAL SYRINGE

REFERENCE TO RELATED APPLICATIONS

This application is a continuation-in-part of my application Ser. No. 07/791,399 filed Nov. 16, 1991 now U.S. Pat. No. 5,364,369, which is a continuation-in-part of application Ser. No. 07/437,203 filed Nov. 16, 1989 now U.S. Pat. No. 5,137,527 which is a continuation-in-part of application Ser. No. 07/072,015 filed Jul. 8, 1987 and now U.S. Pat. No. 4,886,495.

BACKGROUND OF THE INVENTION

1. Field of the Invention

This invention relates to prefilled syringes for use in medical or veterinary treatment.

2. Review of the Art

There has been an increasing trend in recent years to the putting up of pharmaceuticals in dosage forms so as to minimize the preparation required to administer a medicament to a patient and to reduce the chances of dosage errors or contamination. One dosage form which has been gaining rapid acceptance is the prefilled disposable syringe. Various difficulties are however associated with the preparation and usage of such syringes, particularly in the case of preparations which, in ready to use condition, have a short shelf life. Numerous forms of dual compartment syringe structures have been proposed for the shipping of such preparations with components stored in separate compartments for admixture immediately prior to use. Although certain structures have met with some degree of acceptance, they are commonly difficult to manufacture and/or use because of difficulties in filling the syringe with the components, and because they require extensive manipulation immediately prior to use. Moreover they are frequently substantially more bulky than conventional syringes because in many cases they frequently comprise components which effectively represent two syringes in tandem.

Problems in the manufacture of prefilled syringes are not confined to two component systems and even with single component systems the filling of syringes under factory conditions is difficult to mechanize effectively and requires expensive special purpose syringe filling machinery. The same applies to related units prefilled with liquids required for injection or infusion during medical procedures.

Another approach where single component systems are involved is exemplified by British Patent Specifications Nos. 1,252,306 and 1,444,119, and U. S. Pat. No. 4,445,895, in which a prefilled cartridge having a displaceable plug at one end, and a needle penetrable closure at an opposite end, is inserted into the barrel of a syringe for dispensing of its contents. Whilst such cartridges and the equipment for filling them are known and available, they are only really suitable for preparations which can be stored in liquid form, and require either a special or a modified syringe for their use. The cartridges themselves require special filling apparatus.

In a further arrangement disclosed in U.S. Pat. No. 3,845,763, a cartridge or vial is closed at its bottom end by a slidable plug with a downwardly extending stem, which cartridge or vial is inserted bottom end first into a special holder which carries a double ended needle, so that the stem is penetrated by the needle and the body of the vial is converted into a plunger which can be depressed to expel the contents of the vial through the stem. The projecting stem means that the vial cannot be filled utilizing conventional vial filling machinery.

The high capital expenditure involved in implementing known prefilled syringe systems has severely limited their adoption to those few cases where their advantages outweigh the substantial additional unit costs involved as compared to conventional modes of delivery.

SUMMARY OF THE INVENTION

The present invention seeks to provide a system for the distribution of preparations required for injection or infusion in liquid dosage form during medical procedures, which has a wide range of utility both for single component liquid preparations or for two component systems of which one component may be a solid, which utilizes a small number of components all suitable for mass production using material already approved for usage in such applications, which is simple to assemble and can be filled utilizing equipment already available to most pharmaceutical manufacturers, which minimizes the number of "clean room" operations required, and which minimizes certification problems.

The system is based upon and built around a basic component in the form of a 'bottomless vial'. Such a bottomless vial has all of the characteristics of a conventional pharmaceutical vial, except that the glass base of the vial is replaced by a piston wholly received within the vial and designed to form a hermetic seal with its cylindrical side wall, the seal being maintained both when coupled and when uncoupled from a plunger releasably connectable to the piston for moving the latter axially of the vial. A particularly important characteristic of such a bottomless vial is that it can be conveyed, filled and capped reliably by conventional vial sterilization, filling and handling equipment such as is already possessed by most pharmaceutical manufacturers. To this end, the bottomless vial must be free of features which would significantly compromise its stability when handled by such equipment. A flange or bead is required around the base of the vial for various reasons, but must result in no more than a slight increase in the overall diameter of the vial, and must be configured so as to avoid any substantial increase in its tendency to tip when jostled by other similar vials, and the centre of gravity of the vial must not be displaced so far upwardly as to substantially reduce the stability of the vial.

I have found that it is important that the bottom end of such a bottomless vial terminates in a somewhat rounded peripheral bead, which serves several purposes. Firstly, it strengthens the open end of the vial and reduces stress concentrations and the risk of breakage, particularly during insertion of the piston, as well avoiding the danger of glass particles chipping from the edge of the glass which arises in the absence of such rounding. Secondly, the rounding produces a slight internal flare which facilitates piston insertion. Thirdly, it provides means, if sufficiently pronounced, for securely engaging a subsequently applied piston retainer which prevents possible ejection of the piston during shipping and storage of the vial due to gas generation or expansion within the hermetically sealed vial above the piston.

Whilst the provision of a pronounced bead is thus highly desirable, conventional formation of the bead as an external projection on the body has the disadvantage of increasing the diameter of the bottom of the body, thus both increasing the capability of tipping of the vials while being conveyed, and possibly providing a ramp for such tripping by riding over or under the beads of adjacent vials unless the external configuration of the bead is carefully controlled. At the same time, particularly for syringes prefilled with a single component liquid pharmaceutical, there may be a requirement for a syringe capacity which requires the height to diameter ratio of the body to be increased as much as possible, which in turn requires maximum stability of the vial when conveyed free-standing.

The piston must be capable of maintaining a hermetic seal with the wall of the vial, of integrity comparable to that achieved during capping of a conventional vial, and this seal should be maintained in storage and during manipulation of a syringe system incorporating the vial, during which the piston may be subject to non-axial forces transmitted to it by a plunger and tending to break the seal.

In the context of the invention, it should be understood that "vial" refers to a particular type of container, having a rather squat cylindrical body whose height compared to the diameter of its base is such that it may stand stably on its base whilst being conveyed through a vial handling and filling machinery and whilst subsequently sealed and capped. Its body should also be free of external projections large enough to interact with other vials or the filling machinery in a manner such as to promote tipping. A vial has a neck with a large enough internal diameter to permit filling from a vial filling machine: solid filling materials will normally require a larger neck than liquids. Vials should not be confused with cartridges, which are comparatively long and slim, and cannot usually be filled utilizing vial filling machinery since they are too tall to rest in a stable manner on their bases. Cartridges also are typically thin-walled and lack a bead or flange, which renders them fragile, and makes it difficult to insert a piston without excessive risk of breakage.

The differences between such vials and a conventional vial do not prevent them from being filled and capped in conventional vial filling and capping machinery; indeed, apart from the replacement of the bottom wall of the vial by a piston as specified, it is a conventional vial, and can be handled normally by the machinery during filling with either liquid or solid material. The presence of the piston, which is relatively massive, in the lower part of the vial even helps stabilize the latter during filling. Obviously the cubic capacity of such a vial is less than the capacity of a conventional vial of comparable overall dimensions but for most purposes this is immaterial.

The invention provides in one aspect a pharmaceutical vial used for forming a barrel and a piston of a syringe after being filled and capped, comprising a cylindrical glass vial body having at one end an integral open neck and a peripheral external flange around an outer end of the neck, a peripheral rounded edge defining an inner periphery of an open opposite end, and a piston of resilient material having a cylindrical head within and concentric with the cylindrical glass body, the piston maintaining a slidable hermetically sealing relationship with a main inner cylindrical surface of the body, and being located to define a chamber of volume equal to the nominal capacity of the vial between the piston head and the neck of the vial, the piston having integral coupling structure wholly within the body for subsequent connection to a syringe plunger, and the vial being stable when standing on the open end of the body such that it can be conveyed while so standing through vial filling and capping machinery without tipping over, the body being formed adjacent said open end with peripheral radially extending positive retention means for engagement with complementary configurations of a tubular piston retaining member subsequently inserted within said open end of the body to resist overpressure within the body, wherein the retention means is formed by shaping a lower end portion of the body to have a reduced internal diameter such that the retention means is formed by an upwardly facing shoulder at the top of the lower end portion which projects inwardly of the projected circumference of said main interior cylindrical surface, and the lower end portion is located essentially within the projected circumference of a main cylindrical external surface of the body such as to leave the external surface of the body free of projections having an adverse effect on the stability of the vial.

A vial in accordance with the invention may be converted into a syringe by the addition of a plunger coupled to the piston and an outer cap which acts as a needle carrier. More specifically, the syringe includes as well as the vial a syringe plunger connected to the flexible extension from the piston, and an outer cap engaged over the cap of the vial, the outer cap having a hollow needle projecting axially within the cap and a coupling for engagement with injection means and communicating with said hollow needle, the outer cap being axially movable relative to said cap of the vial from a position in which the needle ends short of the cap of the vial to a position in which it penetrates the cap of the vial. The plunger is provided with radially extending flanges for sustaining actuating forces applied to the syringe through a flange grip provided on the outer cap or on a plunger guide or piston stabilizer ring applied to the open end of the vial.

In a syringe for a two component medicament, it is necessary to provide for packaging of the second component and its admixture with the first component in the vial prior to dispensing. The invention thus further extends to a capsule assembly comprising a generally cylindrical sealed capsule having walls formed of a flexible needle penetrable material of suitable properties, a generally cylindrical neck defined by said walls at one end of the capsule, said neck having axially spaced inner and outer peripheral ridges, and a generally cylindrical cap applied to said neck so that a detent within the cap engages the outer peripheral ridge on the neck, a hollow cannula being formed integral with and passing through said cap so that an inner penetrating end within the cap ends short of the neck of the capsule and an outer end in the form of a fluid coupling which extends outwardly of the cap, the cap being displaceable relative to the capsule to a position in which the detent rides over the inner ridge and the inner end of the needle penetrates the neck of the capsule, the cap and capsule being of a diameter such that they can enter the tubular plunger to a position in which a coupling at the outer end of the cannula, is connected to the coupling on the outer cap of the syringe, with the plunger being used as a support for the capsule prior to being coupled to the piston.

Thus the injection system comprises a sequence of components of which various sub-sequences can be combined to form injection systems for preparations requiring shipping and storage as two separate components, certain sub-sequences themselves having utility respectively as injection systems for single component liquid preparations. "Injection" is utilized broadly to cover hypodermic, intramuscular and intravenous injection, gravity and mechanical infusion, and injection into other vessels utilized in medical treatment or testing. For the purposes of description, the "front" or "top" end of an injection system will be considered the end of the system from which a liquid preparation is so injected.

The invention also provides, in a method of producing a prefilled syringe for administering a pharmaceutical preparation, said syringe comprising a generally cylindrical syringe body having a neck at one end and a side wall having a bead finish at the other end, at least a component of the preparation filled into said body, an elastomeric closure closing the body at the neck end and secured by a cap, and an elastomeric piston at said other end forming a hermetic seal with an inside surface of said side wall, needle means for movement relative to the cap to penetrate the elastomeric closure, and plunger means for connection to an outer side of the piston, the improvement wherein the syringe is produced by associating components, including said plunger and said needle, with a prefilled vial produced by forming said body with height to diameter ratio such that the body is stable, and so that any outward extent of the bead is insufficient to result in interference such as would cause tipping, when the body is conveyed standing on said other end through equipment for filling and capping pharmaceutical vials, inserting said elastomeric piston wholly within said other end of the body to form a vial open at the neck, and filling said vial through said neck with said pharmaceutical preparation component, and then applying said elastomeric closure on said cap, whilst conveying the vial standing on said other end through equipment for filling and capping pharmaceutical vials.

Further features of the invention will become apparent from the following description of preferred embodiments thereof with reference to the accompanying drawings.

SHORT DESCRIPTION OF THE DRAWINGS

FIGS. 1 and 2 are elevational and exploded views of a first embodiment of the syringe system;

DESCRIPTION OF THE PREFERRED EMBODIMENT

Figure 3:
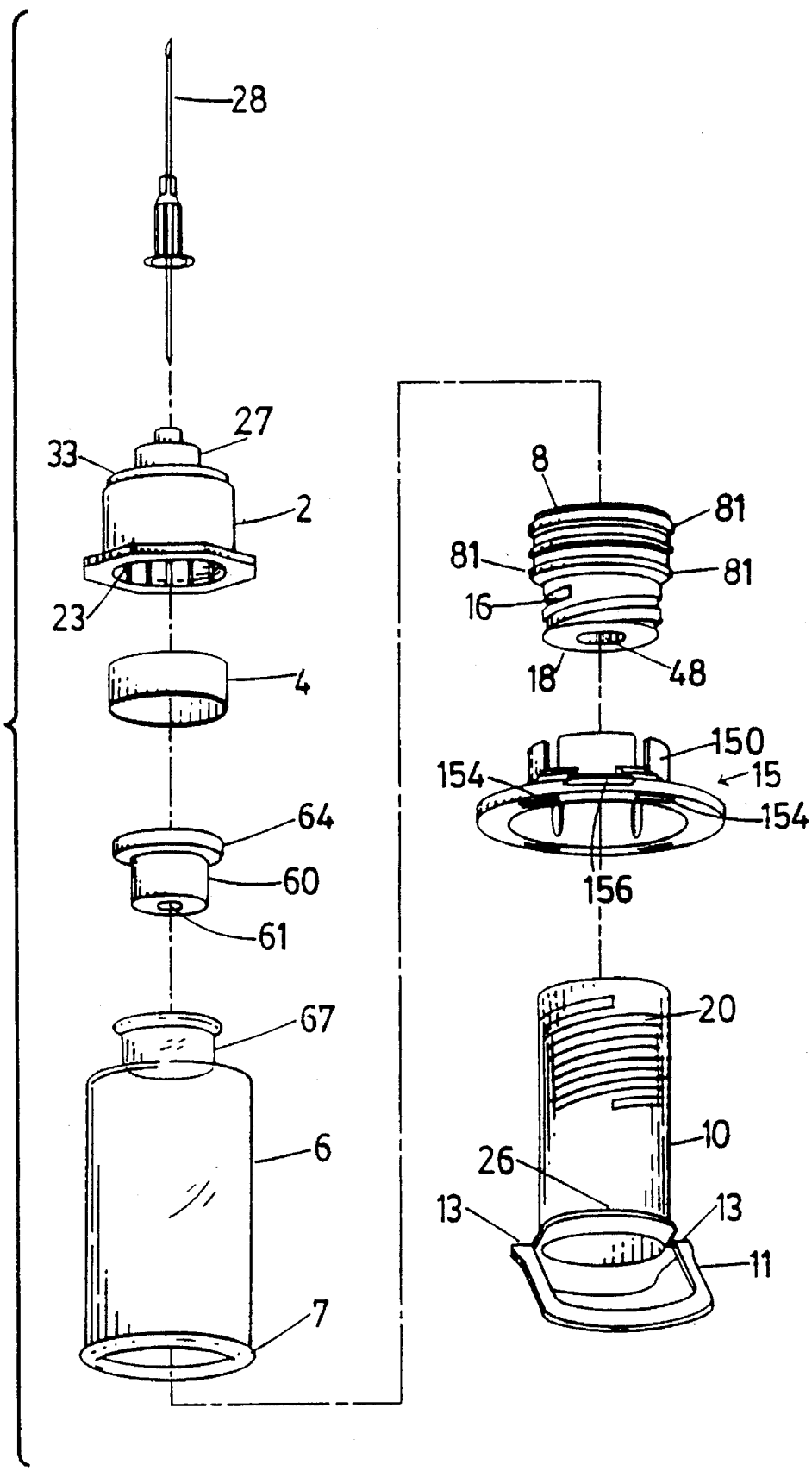
FIG. 3 shows the separated parts of a modified embodiment of the syringe system.

Referring to FIGS. 1 and 2, a syringe system for the injection of a liquid preparation stored as two components comprises seven primary mechanical components, apart from the components of the preparation. The components of the preparation typically comprise a first component A which may be in any physical state suitable for storage in vial, and a second liquid component B, typically but not necessarily sterile water. The liquid component B is stored in a sealed capsule 14 of flexible material, manufactured using conventional techniques from a material, usually synthetic plastic, which is compatible with the contents of the capsule. The first component is stored in a cylindrical vial 6, typically of glass, and capped by an annular cap 4 which retains a conventional needle penetrable sealing member accessible through a central opening in the cap. By a vial is meant a cylindrical vessel which can assume a stable upright position supported by its base, the overall height of the vessel exceeding the external diameter of the rim of its base by a factor sufficiently small that it remains stable when passing through conventional vial filling and capping equipment utilized to fill and cap the vial. This factor preferably does not exceed 2.5 for the present embodiment, but can be increased by means discussed further with reference to FIGS. 7–13. A neck 5 at the upper end of the vial 6, which is capped by the cap 4, has a relatively internal diameter characteristic of such vessels, usually not less than about 7.5 mm for liquid or 10 mm for solids, so that filling with either liquids or solids can be readily achieved. The cap 4 is formed by an aluminum sleeve, having a flange retaining a sealing member formed by a soft rubber disc or plug 5 over or in the front end opening, and tightly crimped onto a neck at the front end of the vial so as to seal the latter. A major difference from conventional vials is that the conventional bottom wall of the vial is replaced by an axially movable piston 8 wholly within the vial and in sealing contact with the vial walls. When received within the vial 6, this piston in no way interferes with the handling of the vial using conventional machinery, and in particular permits the vial to be stood on its base with its neck (5) (which forms the front end of the vial when in use) upwards as it passes through the filling and capping equipment.

The filled vial 6 may be converted into a prefilled syringe by applying an outer cap 2 over the cap 4 and positively attaching a cylindrical plunger sleeve 10 to the piston 8. The piston 8, typically formed of rubber, is moulded with a rearward extension 16 with an external thread 18, while the interior of the front end of the plunger sleeve 10 is formed with a complementary internal thread 20 (see FIG. 3) so that it may be screwed onto the piston 8. A recess 48 (see FIG. 3) may be formed in the extension 16 to increase its flexibility. The outer cap 2 fits over the inner cap 4 so that a hollow needle 22 (see FIG. 6) formed within the cap 2 does not reach the penetrable zone of the cap 4. On the front of the cap 2 and in communication with the hollow needle 2 is a coupling adapter 27, for example similar to those sold under the trade mark LUER-LOK, for connection of the syringe to a needle 28 or other instrumentality (see FIG. 3). To prepare the syringe for use, the outer cap 2 is pulled back over the inner cap 4 so that the needle 22 penetrates the cap, and the needle 28 or other instrumentality is applied. This should be done without pressing on the plunger sleeve so as to avoid accidental ejection of the contents of the syringe. The rear ends of both cap 2 and the sleeve 10 are formed with radially extending flanges 24 and 26 respectively which form finger grips for operation of the syringe. Thus if a user grips the assembled syringe by the flanges and presses them towards each other, the contents of the syringe can be expelled through the needle 22 and the needle 28. It will be noted that the rear end of the vial 6 is formed with only a relatively slight external bead 7 rather than the wide finger flange commonly found on the barrels of conventional syringes. In the present arrangement, the flange 24 provides the function of such a finger flange, enabling the bead 7 to be reduced to a size which will avoid such interference between the flanges of adjacent vials as would cause tipping when the vials are conveyed in a vertical attitude through filling and capping equipment.

In many applications, it is desirable to prevent premature penetration of the plug 5 by the needle 22, and therefore the cap 2 may be moulded with short internal threads (not shown) which prevent rearward movement of the cap 2 unless it is twisted so that the threads bite into the soft aluminum of the cap 4 and draw the cap 2 rearwardly so that the needle 22 can penetrate the plug.

A prefilled syringe constructed as discussed above has significant advantages over conventional prefilled syringes in that the vial may be filled using conventional vial filling equipment, and yet may be utilized directly instead of requiring its contents to be transferred to a syringe prior to use as has been conventional in the use of vials.

The vial may also be charged with material which is not directly injectable, such as solids which must be dissolved or suspended in a liquid medium prior to injection. In this case the liquid medium is sealed as already described in a flexible capsule 14. A third cap 12 is applied to the capsule as shown in FIG. 2, which is inserted into the plunger sleeve 10 so that a screw thread 30 on the exterior of the cap engages screw thread 20 within the sleeve.

A neck 34 of the capsule 14 (see FIG. 4) has two peripheral ridges 36 and 38. As the cap 12 is applied to the capsule, a detent 40 within the cap is pushed over only the outer ridge 38 so that a hollow needle 42 mounted in the cap stops short of the end of the capsule. By forcing the detent 40 rearwardly over the ridge 36, the needle 42 can be forced rearwardly so as to penetrate the capsule.

The conduit in the needle 42 extends through the cap 12 into an extension 70 which is configured at its outer end to couple with a standard syringe coupling such as the coupling 27 on the cap 2. This enables the capsule 14, once inserted in the plunger 10, to be locked through the extension 70 and the coupling 27 to the cap 2 to produce the compact assembly shown in FIG. 1. The inner end of the plunger 10 is a press fit on an annular retaining flange 33 formed on the cap 2. To prepare the syringe for use, the cap 2 is forced rearwardly over the cap 4 so that the needle 22 within the cap 2 pierces the seal 5, and the capsule 14 is forced forward so that it is pierced by the needle 42 and its contents can be expelled through the needle 42, the extension 70, the coupling 27 and the needle 22 into the vial 6. The assembly of the capsule 14 and the plunger 10 can then be released from the remainder of the syringe by turning so as to release the extension 70 from the coupling 27, a needle (see FIG. 3) may be applied to the coupling 27, the capsule 14 is removed from the plunger 11 and discarded, and the plunger 11 is screwed onto the coupling 18 to ready the syringe for use.

Figure 5:
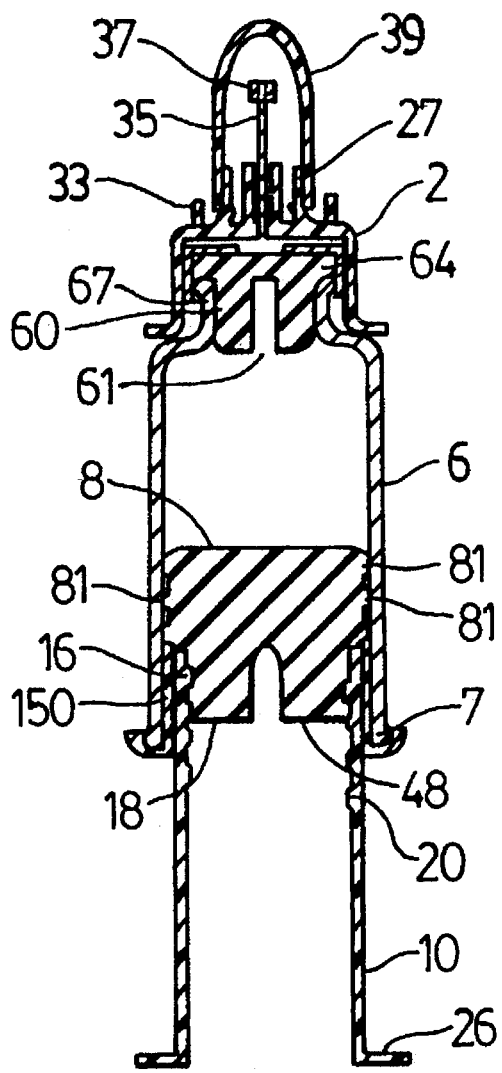
FIG. 5 is a longitudinal cross section through the assembled system of FIGS. 3 and 4.

A similar arrangement may be utilized for single component medicaments in which case the capsule 14 and cap 12 are not provided. The arrangement is advantageous for both single and multiple component medicaments since only the vial need be assembled and filled in a clean room, the only additional step required over the filling of a conventional vial being the insertion of the piston 8. The plunger 10 may be pressed onto the cap 2, and this assembly, if desired together with a needle and/or a capsule 12 and cap 14, may be separately sterilized and packaged, without endangering the stability or destroying the contents of the vial, which will often be sensitive to heat or radiation utilized for sterilization purposes. Since the capsule 12 can withstand conventional terminal sterilization techniques (see further below), it can be sterilized independently of the vial. This is a major advantage over many two-component syringe systems in which the components are separated only by some form of penetrable plug or diaphragm and must therefore either be fully assembled in a clean room, or subjected in assembled form to terminal sterilization techniques which may destroy or damage a component of the pharmaceutical preparation.

Where the capsule 12 is not being used, it is possible to utilize a cap 2 in which the needle 22 is not provided, and instead use a needle arrangement as shown in FIG. 3 or FIG. 5.

Figure 4:
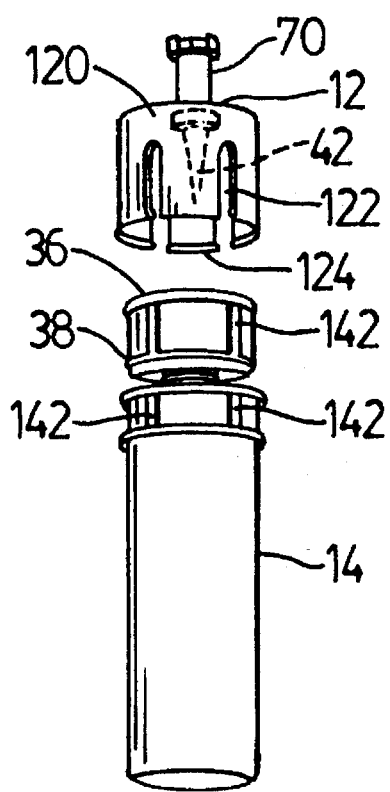
FIG. 4 shows, separated, a diluent capsule and cap for use with the system of FIGS. 1 and 2 or 3.

Further features of the invention are shown in FIGS. 3–5. The same reference numerals are used to denote the same parts in these figures as in the previous figures, where applicable, and construction and operation are similar except where otherwise indicated.

FIGS. 3–5 show a vial and syringe system according to the invention, the vial comprising a body 6 of rigid transparent material, usually glass although synthetic plastic resins might be utilized in certain applications. The body has the general configuration of a conventional vial except for the absence of a bottom wall. In order to compensate for the strengthening effect which would be provided by the bottom wall, in order to provide a detent for an optional plunger stabilizer ring 15 described further below, and in order to permit a slight flare at the extreme bottom end of the vial, a rounded bead 7 is provided around the perimeter of the bottom end of the body, although its peripheral extent should not be sufficient to increase substantially the diameter of the vial or decrease substantially its stability during handling.

A medicament A is retained within the vial by a piston 8. A closure 60 substantially fills a neck portion 67 of the vial after the vial, closed at the bottom by the piston, has been filled through its neck portion by a conventional vial filling machine. Although the medicament shown is a solid, it may be a liquid, or filled as a liquid and lyophilized to leave a solid residue. The piston 8 is moulded from rubber, preferably of at least 50 durometer hardness, and is formed with multiple, preferable three, peripheral ribs 81 on its outer surface, the external diameter of the ribs being slightly greater than the internal diameter of the body 6 so that an hermetic seal is established when the piston is pressed into the bottom of the body, initial entry being assisted by the flare mentioned above. The piston is moulded as a substantially solid body so that it has sufficient rigidity to maintain the desired hermetic seal with the body, any central bores within the piston (see FIG. 5) required to assist needle penetration being of insufficient radial extent to have any significant effect on its rigidity. Although in the piston shown in FIG. 6, a central bore 48 does just extend into the piston proper, its axial extent within the piston and its diameter are sufficiently small relative to the piston diameter that the rigidity of the piston is not substantially reduced.

The piston has a downward extension 18 of reduced diameter, in which the bore 48 is also present. The diameter of the bore 48 forms in this case a greater portion of the diameter of the extension 18, whose flexibility is thus somewhat increased by its presence. The extension carries on its outer surface a multistart thread, defined by grooves 16 which terminate abruptly short of the piston, forming abutments serving a purpose discussed further below. Provided that the hardness and rigidity requirements for the piston as a whole are met, the rubber utilized to form the piston, and any external coating on the rubber (which may act to increase the effective hardness of the rubber), are selected for compatibility with the medicament contained in the syringe, a number of approved materials being available and well known in the pharmaceutical art.

The neck closure 60 may be formed of similar rubber. After insertion of the closure 60, its flange 64 may be held in place by a conventional cap 4 crimped over the flange and a flange on the neck of the bottle. Such a cap 4 may have a flip-off top attached to a separable central portion of the cap, partially severed from the remainder of the cap so that these portions may be broken away prior to assembly of the syringe to expose a central needle penetrable zone of the closure 60 above the bore 61.

The piston together with its extension 18 is relatively massive, with a weight which typically amounts to at least a major portion of that of the body 6. This weight in the lower part of the body assists in stabilising the vial during handling and filling and further inhibits tipping.

As mentioned above, vial assembly and filling will normally be performed in a clean room, since many pharmaceuticals will not withstand terminal sterilization procedures. The only additional step which requires to be carried out in the clean room other than is conventional in the filling of vials is the insertion of the piston 8.

In order to convert the basic vial into a syringe system, the procedure described with reference to FIGS. 1 and 2 may be used. Only the differences will be described in detail for this embodiment. FIG. 3 shows the components of a syringe system separated, while FIG. 5 shows them assembled and sectioned (although an alternative needle arrangement is shown in FIG. 5). It should be understood that the diluent cartridge 14 and cartridge cap 12 as shown in FIG. 4 are optional features of the system and will only be utilized when a diluent or solvent is required for the content of the vial which is not provided by some other means.

Figure 6:
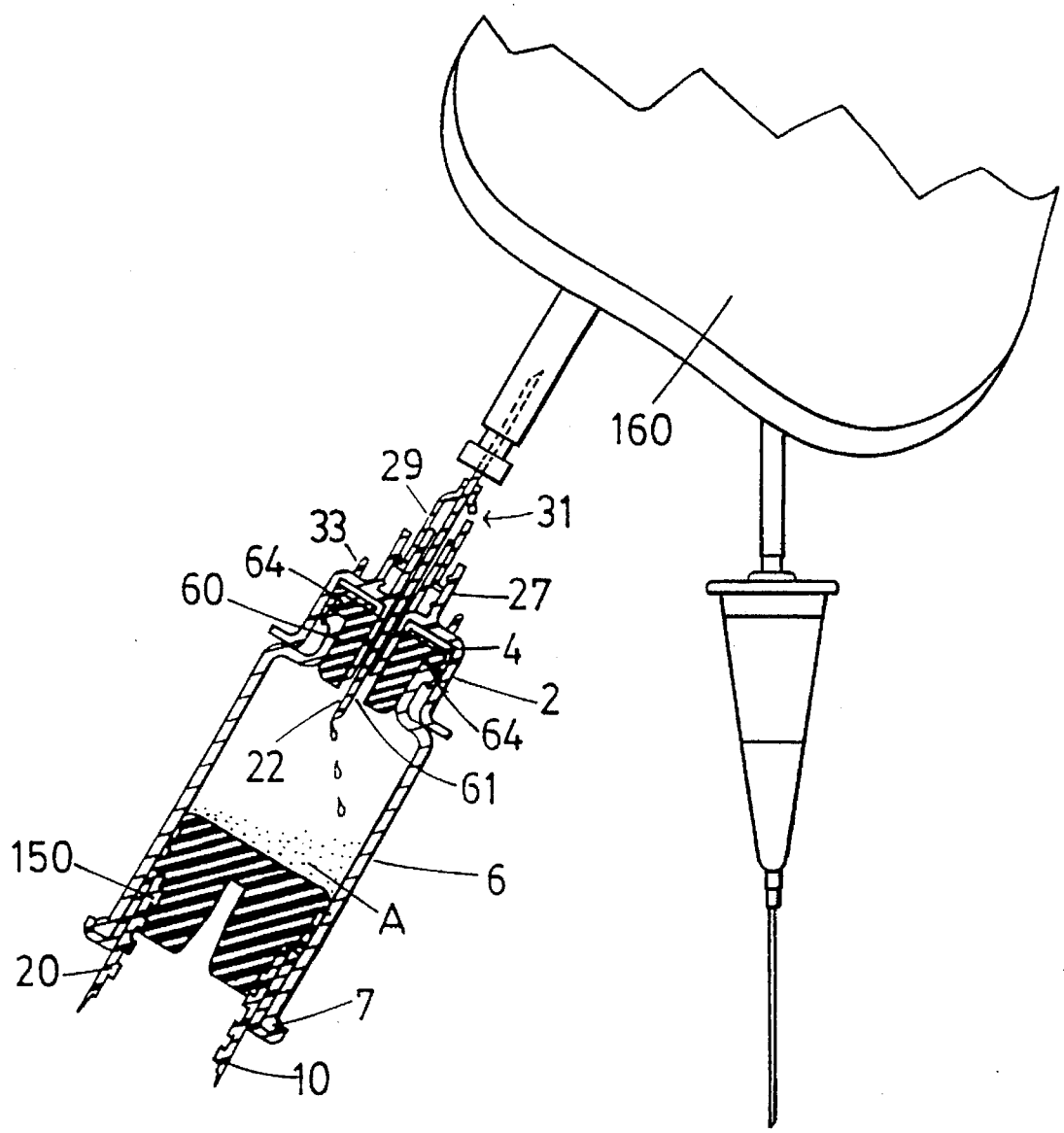
FIG. 6 is a fragmentary view of a syringe in accordance with the invention utilized in conjunction with an I.V. bag.
Figure 13:
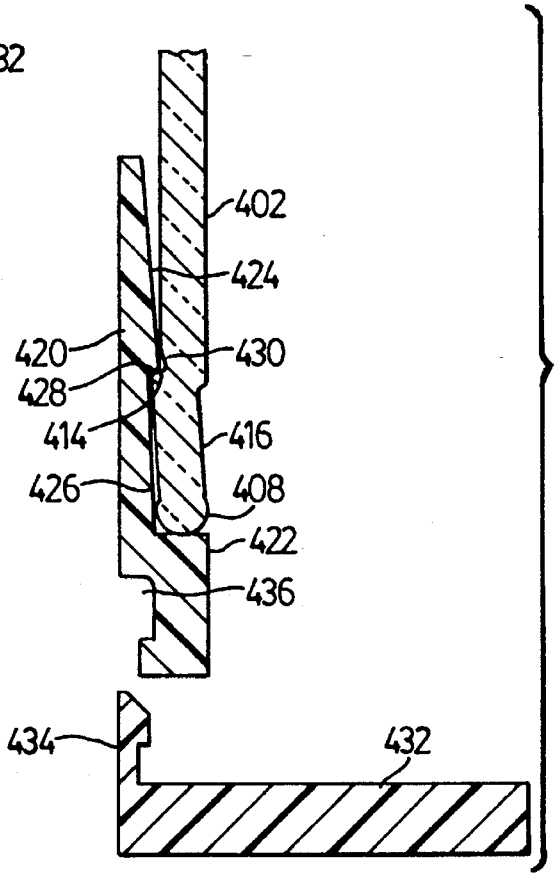
FIG. 13 is a detail of the body and retainer ring shown in FIG. 12, on an enlarged scale.

Referring to FIGS. 3 and 5, an outer cap 2 is pushed over the cap 4, and is similar to that shown in FIG. 2, except that the internal needle 22 shown in FIG. 6 is omitted, the syringe being utilized with an alternative needle arrangement. In FIG. 13, a conventional double ended needle 28, is shown, the inner end of which replaces the needle 22.

FIG. 5 shows an arrangement in which the needle 28 may be single ended, an auxiliary hollow needle 35 being provided with a cylindrical sleeve 37 at the top which replaces the outer extremity of the inner portion of the coupling 27. A cap 39 is provided to retain the needle 35 within the coupling 27 until the needle 28 is fitted. When the syringe is to be used, the cap 39 is removed, and the sleeve of the needle is placed over the sleeve 37 and pushed down so that the needle 35 can penetrate the top of the vial and the needle 28 can be engaged with the coupling 27.

These needle arrangements are preferred for a syringe which is shipped in an essentially ready-to-use form, since the cap 2 may be pushed fully onto the cap 4 during assembly, yet the closure 60 remains unpenetrated until the needle (or other instrumentality as discussed below) is fitted at the time of use. On the other hand, the integral needle 22 is convenient where the assembly is to be utilized in the manner shown in FIGS. 1 and 2 and a capsule 12 is utilized. The inner surface of the cap 2 is provided with longitudinal ribs 23 which indent the soft aluminum of which the cap 4 is typically fabricated, and help retain the cap 2. The portions 41 and 43 of the cap 4, if present, are of course broken away prior to application of the cap 2.

The cap 4, closure 60, vial body 6 and piston 8 have already been described in detail above. The plunger 10 differs from that shown in FIGS. 1 and 2 in two respects. Its internal threads 20 end abruptly at abutments short of the front end of the plunger, so that when the plunger is screwed onto the extension of the piston, the abutments at the ends of the threads meet abutments at the ends of the external grooves on the extension which grooves in this embodiment stop short of the inner end of the extension, just before the inner end of the plunger contacts the rear surface of the piston. This prevents the plunger being screwed excessively tightly against the back of the piston in a manner which might result in rocking movements of the plunger being transmitted directly to the piston. Instead such movements are largely absorbed by the flexibility of the extension 18. Secondly, the flange 26 at the rear end of the plunger is moulded so that about one half of its periphery is separated into an integral loop 11, which can be flexed rearwardly about hinge lines 13, and serves either as a thumb loop to assist manipulation of the syringe, or a suspension loop from which the syringe can be hung during infusion of its contents as discussed further below. The synthetic plastic material from which the plunger is moulded is selected from those having hinge forming capability such as many pharmaceutically acceptable grades of polypropylene.

In order to provide further stabilization of the plunger, to prevent its withdrawal from the body, and to provide a finger grip during manipulation of the syringe, particularly where longer vial bodies 6 are utilized, an optional plunger stabilizer and adapter ring 15 may be provided. This has axially extending inner flanges 150 which enter the inner end of the body, and retaining lugs 152, which snap over the bead 7. Openings 154 and flanges 156 may be provided on the rear surface of the ring, as required, to assist in adapting the syringe to infuser apparatus.

Where the contents of the vial are liquid and do not require reconstitution or dilution, or reconstitution is effected by a diluent or solvent introduced via a needle or cannula through the closure 60, the cartridge cap 12 and diluent cartridge 14 are not required, the components already described constituting a complete syringe system. Otherwise these components may be provided and utilized as already described in relation to the embodiment of FIGS. 1 and 2. The components themselves are however somewhat modified as shown in FIG. 4, to facilitate handling. A skirt portion 120 of the cap is formed with longitudinal slots 122 extending from its rear edge, and inner lips 124 around the inner periphery of that edge, whilst a front extension of the cartridge 14 is provided with ribs 142 extending longitudinally between the peripheral ridges 36 and 38, which ribs are accommodated by the slots 122. The ribs 142 are continued beyond a peripheral groove behind the ridge 36. The threads 30 and the cap 12 are reduced to short ridges between certain of the slots 122. Because of the slots, the cap 12 is readily engaged over the ridge 38, but when the assembly is inserted into the interior of the plunger 10, the diameter of the cap relative to the internal chamber of the plunger 13 such that the lip 124 is pressed into the ring of shallow recesses defined between the ridges 36 and 38 and the ribs 142, thus ensuring that the threads 30 may be engaged with the threads 20 within the plunger by turning the capsule, and inhibiting accidental forward movement of the cartridge 14 into the cap 12.

The capsule 14 is blow moulded from a heat sealable, film grade, low melting, high ethylene random propylene-ethylene copolymer suitable for medical use. An example of such a material, already approved for pharmaceutical applications, is DYPRO (trade mark) polypropylene Z9350 from Fina Oil and Chemical Company which has a melting point of about 130° C. Such a material, formed by injection of ethylene into a propylene matrix, combines necessary qualities of transparency, impermeability and flexibility with the stability to withstand sterilizing temperatures in an autoclave, despite its low melting point; the pressure in the autoclave is maintained at a sufficient level to prevent bursting of the capsule during sterilization. Conventional capsule materials are unsuitable for use in this application, since they lack at least one of the necessary properties of flexibility, transparency, impermeability, penetrability, compatibility with conventional pharmaceutical diluents, and ability to withstand sterilization temperatures without failure or degradation.

Utilization of syringes incorporating the above described modifications is similar to that already described. With a small modification to certain of the syringe components, the syringe contents may be reconstituted or diluted with fluid from an I.V. bag or minibag 160 and then injected into the bag for delivery, as shown in FIG. 6. Both the inner and outer components of coupling adaptor 27 of the cap 2 are elongated, and the bores of the inner component of the coupling adaptor and of the needle 22 are sufficient to provide an air venting passage around the read end of the needle 22 when fitted to the adaptor 27. A locking sleeve 29 on the needle 22, which sleeve engages the adaptor 27, is provided with a ventilation opening 31, such that when the sleeve 29 is screwed partially onto the adaptor as shown, air can escape through the sleeve as fluid from the bag 160 enters the syringe through the needle 22. When a desired amount of fluid has entered the syringe, the ventilation opening is closed by screwing the needle further onto the adaptor, following which the contents of the syringe may be injected into the bag 160.

Referring to FIGS. 7–10 of the drawings, a syringe comprises a syringe barrel in the form of a somewhat elongated glass vial 202, of which the bottom wall is absent apart from a slight inward projection of a strengthening bead 206 formed at the bottom of a side wall 204 of the vial and best seen in FIG. 20. In the example shown the strengthening bead 206 also has a very slight outward projection, but this is far smaller than would be necessary if the bead were formed wholly externally of the side wall 204, and may be entirely eliminated. In any event, the outward extent of the projection should be insufficient to prevent vials from standing very closely adjacent to one another without sufficient space to tip. Typically the projection will not exceed about one fifth of the total thickness of the bead. The projection of the bead on the inside should also be limited, both so that the head 210 of 1a moulded rubber piston 208 can be inserted into the vial past the projection (this is facilitated by the presence of peripheral grooves 212 in the head between sealing lands 214), and so that a sleeve 218 of a combined finger grip, piston stop and plunger guide 216 (henceforth referred to as the finger grip) can be pushed past the projection whilst remaining a snug fit within the side wall of the vial. Insertion is facilitated by the slight flare provided at the bottom entry to the vial body by the rounding of the bead, and the insertion is readily mechanized.

The piston 208 is also provided with an integrally moulded downward extension 220 which is formed with a central cavity 223 to increase its flexibility relative to the head 210 of the piston which is substantially solid. The piston is dimensioned so that when it is inserted in the vial 202, the lands 214 are compressed sufficiently to form a hermetic seal against the interior of wall 204 whilst permitting the piston to be moved longitudinally of the vial. Initially, the piston is located at the bottom of the vial (see FIG. 8), with the bottom of extension 220 just within the vial so that it does not affect the ability of the vial to stand upright on its base formed by the bead 206. The location of the fairly massive solid rubber piston 208 at the base of the vial helps stabilize the empty vial 202, even when the height of the latter is somewhat greater relative to its diameter than is normally required for stability. The practical limit of the height to diameter ratio is set entirely by the requirement that the vials can be conveyed through a conventional vial filling and capping machine in a sufficient stable manner to permit reliable operation of the machine. In the example shown, the vial has an outside diameter of approximately 3 cm and a height of 12.8 cm for this diameter. A height of 14 centimeters is believed to approach the practical limit for stability, but this ratio will vary somewhat according to the relative wall thickness of the vial and the weight of the piston. Provided that the outward projection of the bead 206 is insufficient to affect stability, so that the vials can jostle without applying tipping force to each other, and assuming use of a piston generally as described, the maximum ratio attainable should be greater than 4, but will be less than 5.

Figure 9:
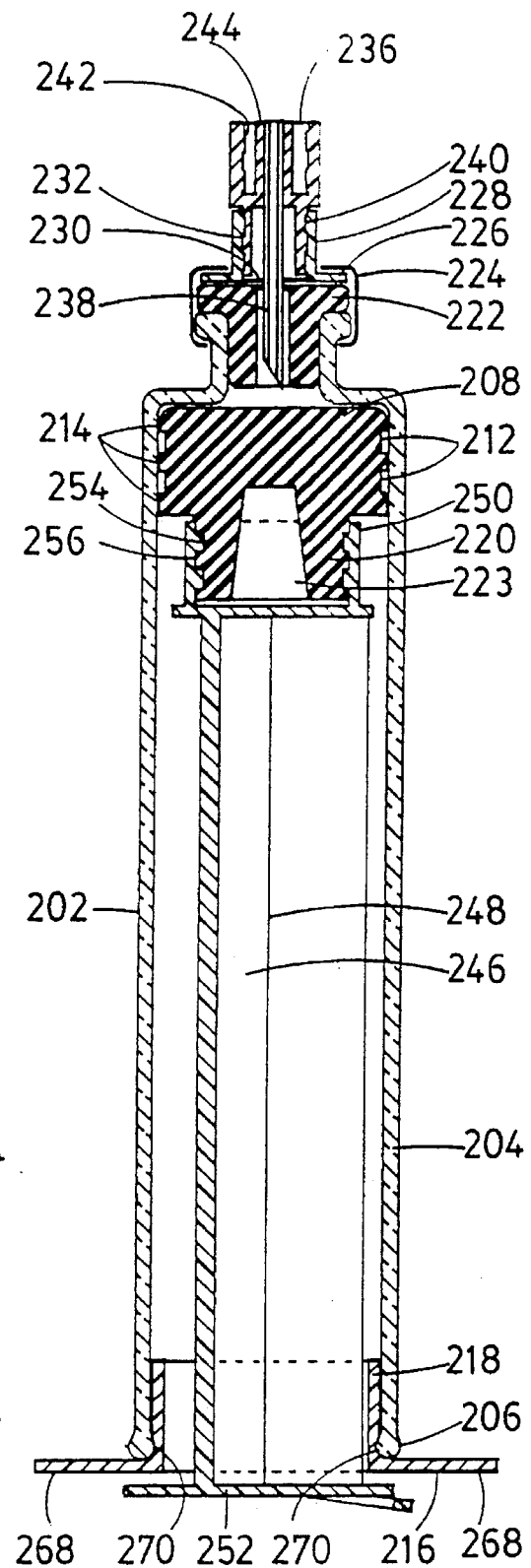
FIG. 9 is a longitudinal section through an assembled syringe, after discharge of its contents.

The stopper 222 and cap 224 applied by the conventional vial filling and capping machinery may be of conventional construction, although the stopper 222 is preferably designed substantially to fill the neck of the vial so as to minimize dead space above the piston when the latter is pushed to the top of the vial (see FIG. 9). This ensures that as much as possible of the contents of a syringe formed from the vial can be expelled by movement of the piston.

Figure 10:
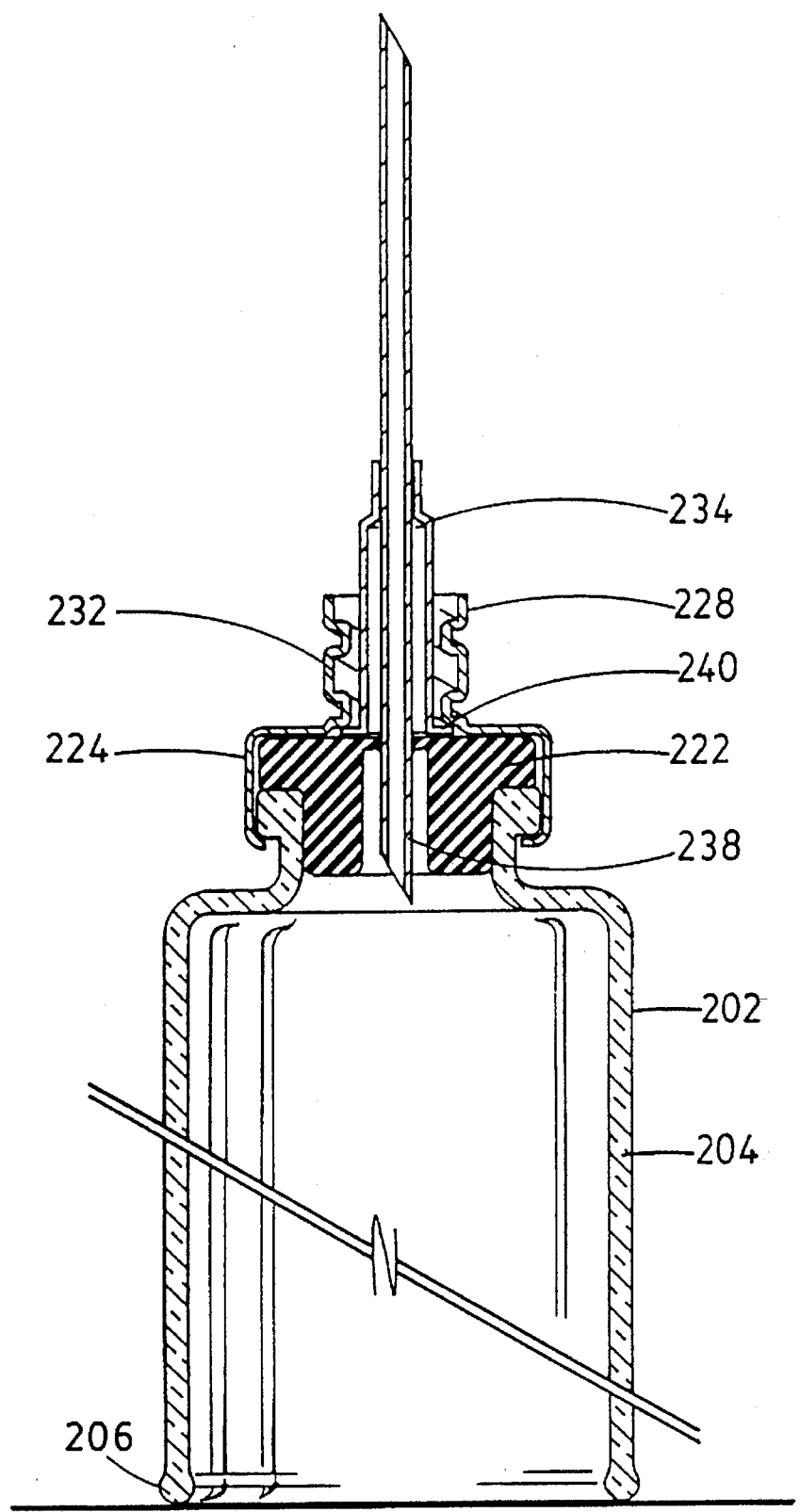
FIG. 10 is a fragmentary longitudinal section on an enlarged scale of a portion of the syringe shown in FIG. 9, showing a modification of the arrangement shown in that Figure.

The cap 224 is preferably modified as shown in FIG. 9 and FIG. 10. In FIG. 9, a conventional main cap cooperates with a moulded plastic adaptor assembly comprising an annular flange 226 within the cap, a cylindrical extension 228 extending through the cap and a thin diaphragm 230 closing a bottom end of the extension. An internal thread 232, similar to that provided on conventional syringe adaptors for receiving needles, such as those sold under the trade-mark LUER-LOK, is formed within the adaptor. A removable push on cap may be provided to close the open end of the adaptor during storage, being removed prior to use. In FIG. 10, the cylindrical extension 228 is formed integrally with the aluminum cap, again with an internal thread 232. I have found that the extension 228 can be accommodated by conventional vial capping machinery, at any rate with no more than minor modification, without interfering with the capping process, whilst the provision of such an extension enables the elimination of a separate adaptor cap, and the additional assembly step required to apply it.

In order to convert the vial into a syringe, either a double ended needle 234 of the blood collecting type may be applied directly to the extension 228 (see FIG. 10) or an adaptor 236 (see FIGS. 7 and 9) may be provided for any needle or alternative delivery device equipped with a standard syringe coupling so as to provide the latter with the capability of penetrating the stopper 222, as well as the diaphragm 230 if present. The adaptor 236 has a needle 238 and external thread 240 at one end, the needle providing the penetration function and the thread 240 engaging the thread 232, while its other end provides an internally threaded socket 242 and coaxial spigot 244 for forming a fluid-tight coupling to the needle or the like.

Prior to fitting the double ended needle 234, or needle and adaptor 236, a plunger 246 is applied to the extension 220 of the piston. The plunger has a shaft 248, of cruciform cross-section in the example shown, an internally threaded sleeve 250 at its one end, and an end flange 252 at its other end. The sleeve 250 has internal multistart threads 254, complementary to external multistart threads 256 on the extension 220. The lands between the threads 254 on the sleeve 250 and the threads 256 on the extension 220 both stop short respectively of the outer end of the sleeve 250 and the inner end of the extension 220 so as to form abutments 258, 260 which prevent the sleeve 250 from being screwed tightly against the underside of the head 210 of the piston. This means that any tilting forces applied to the plunger are applied to the relatively flexible extension 220 and not directly to the head 210, thus minimizing the risk of breaking the hermetic seal between the head 210 and the vial.

The plunger is formed of a hinge-forming synthetic plastic such as a pharmaceutical grade polypropylene, and a generally semicircular peripheral portion 262 of the flange and is separated from the remainder of a slot 264, remaining connected only by thin, hinge-forming connections 266. This portion 262 provides a finger loop which can be pulled rearwardly, as shown by broken lines in FIG. 1, to facilitate handling of the plunger. As a supplemental or alternative feature, a notch 272 may be formed in the shaft 248 of the plunger, to provide a hook by means of which the syringe may be suspended when used in certain infusion applications.

In order to provide the various functions of preventing total withdrawal of the piston, forming a guide for the plunger and restricting its tilting movements, and providing a finger grip for the user, the combined finger grip and retainer 216 is pressed into the bottom of the vial 202 after filling and capping of the latter. It comprises the sleeve 218 and a peripheral flange forming oppositely extending finger grips 268. It is also moulded from a pharmaceutical grade of plastic such as polypropylene. The sleeve 218 is a resilient press fit in the open end of the vial 204 so that it is slightly compressed by the internal projection of the bead 206 during insertion. Insertion of the retainer 216 may be facilitated by moderate warming of at least the retainer, and the slight flare provided by the rounding of the bead 206 also facilitates insertion. Beneath the grips 268 the sleeve has shallow arcuate grooves 270 in which the bead 206 snaps as the sleeve is pressed home. Forces applied to the grips 268 tending to pull the sleeve 218 away from the vial in turn tend to deform the sleeve, in such a manner as to increase the grip of the grooves 2700 on the bead thus resisting withdrawal of the sleeve.

Figure 7:
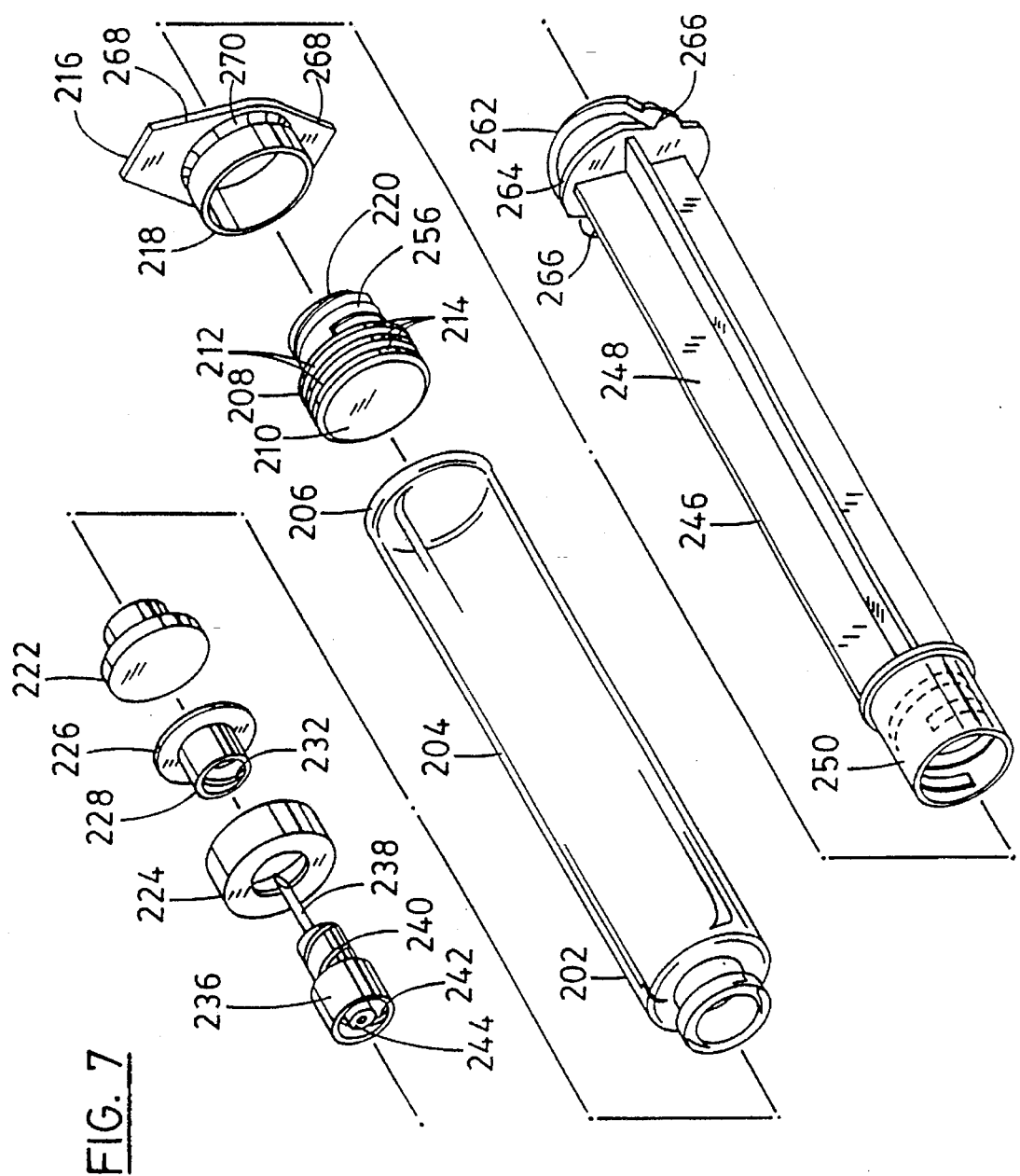
FIG. 7 is an exploded isometric view of the components of a further embodiment of syringe.
Figure 8:
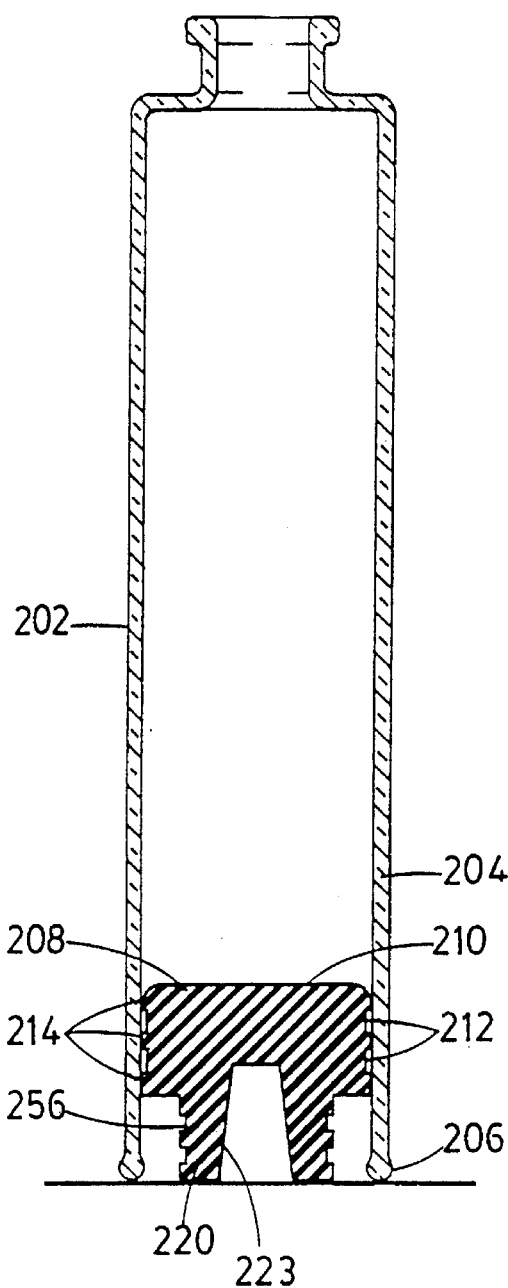
FIG. 8 is a vertical section through a vial portion of the syringe of FIG. 7, ready for filling.

During manufacture, the empty vials 204 are conveyed through a conventional sterilizing station, the piston 208 is inserted in each vial 204, and the latter is filled and capped utilizing conventional vial filling and capping machinery (but preferably using a modified cap as shown in FIGS. 7 and 9 or FIG. 10). The guide and finger grip 218 is then pressed into the base of the vial, which is shipped with the plunger 246 unattached. Prior to use, the plunger 246 is screwed onto the piston, and a needle or the like is applied to the extension 228, utilizing an adaptor 236 if necessary so as to penetrate the stopper 222, at which point the syringe is ready for use.

Figure 11:
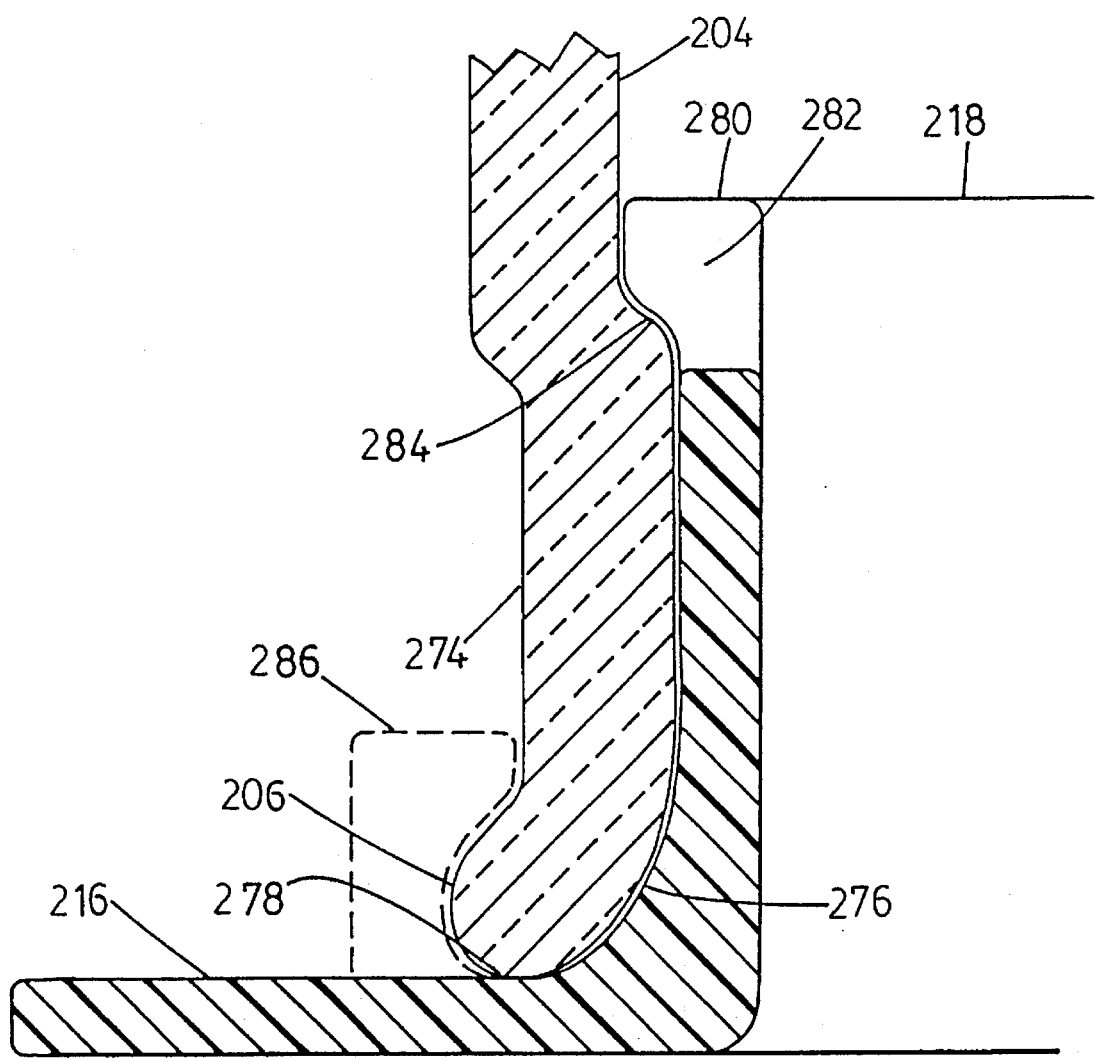
FIG. 11 is an enlarged vertical section through the bead of a modified embodiment of the syringe, also showing adjacent parts of a modified piston retainer and finger grip.

A modified configuration of the bottom end of the vial body is shown in FIG. 11, in which an alternative approach is utilized to bringing the bead at the bottom end substantially within the diameter of the cylindrical vial body. Peripheral beads around the openings of glass bodies of this type are conventionally formed by flame softening the glass and adjusting the positioning and profile of the bead by rolling the body against suitable forming surfaces. In the FIG. 5 embodiment, a bottom portion 274 of the body 204 is flame softened and rolled so as slightly to reduce its diameter over about a length of typically 5–6 mm, and a fairly conventional out-turned rounded bead 206 is formed by flaring the bottom of this reduced diameter section. The reduction in diameter is such that at least the greater part of the bead is within the general diameter of the body. In the example shown, the outside diameter of the bead is very slightly greater than the general outside diameter of the body but this need not be so. In a typical example, the inside and outside diameters of the main portion of the vial body are 27 mm and 30 mm respectively, providing a wall thickness of 1.5 mm, and the reduction in diameter at the bottom is about 1 mm. The bead can then be formed by flaring the bottom end of the vial without increasing the outside diameter of the bead significantly beyond that of the main portion of the vial and typically by no more than 0.5 mm, even though a significant flare 276 can be provided and, because of the flare, the bottom contact line 278 of the vial when freestanding on a plane surface is substantially coincident with the outside diameter of the main body 204 of the vial, thus maximizing stability. Juxtaposition of the vial bodies in the event of jostling on a line will prevent any ramping tendencies which might otherwise occur with a flared bottom configuration of this type.

Whilst the presence of the piston after its insertion in the vial body acts to introduce a substantial mass which trends to stabilize the vial, the mass of the piston relative to that of the vial body will decrease as the height of the latter increases. Nevertheless it will result in a smaller rise of the centre of gravity of the assembly as the vial becomes higher than would otherwise be the case. It is also desirable that the vial bodies be stable without the piston present so that they may be conveyed through a stabilizer prior to insertion of the pistons. The present invention is particularly valuable in this respect since the disturbing influence of a bead at the open end projecting beyond the diameter of the main portion of the body is particularly severe under such conditions.

In order to cooperate with the modified vial body profile, the finger grip/retainer 216 must also be modified. The groove 270 is replaced by a bead 280 at the upper end of the cylindrical portion 218, which bead may be moulded with a taper and if necessary with slots 282 to facilitate insertion, and/or the component 16 may be warmed to facilitate insertion. The bead must retain the component with sufficient tenacity to withstand pressures from the piston which may be developed through pressure build-up in the vial during normal storage, although it should be noted that pressure of the piston on the bead may actually help retain it by forcing it against the shoulder 284. Alternatively or additionally, claws 286 may be moulded onto the component 216 to retain it by external engagement with the bead 206.

Figure 12:
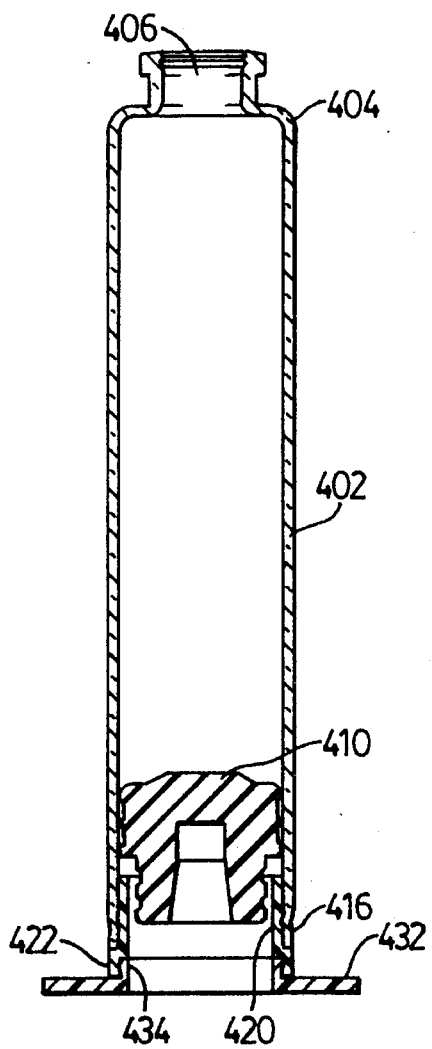
FIG. 12 is a longitudinal section through the body of a further embodiment of bottomless vial, shown fitted with a piston retainer ring.

A further development of the embodiment of FIG. 11 is shown in FIGS. 12 and 13. A body 402 for a bottomless vial is moulded from glass or synthetic plastic material, with a generally cylindrical form having shoulders 404, at the top end connecting to a hollow neck 406. At a bottom end of the body its side wall is formed with a rounded or beaded bottom edge 408 to form an open bottom end through which a piston 410 may be inserted.

A portion 416 of the inside side wall adjacent the bottom edge 408 is tapered inwardly and joined to the remainder of the side wall by a peripheral jog 412 so as to provide a narrow internal upwardly facing annular shelf or shoulder 414 above a funnel-shaped upwardly tapered bottom entry to the interior of the body. The shelf and tapered bottom entry may be formed by rolling a heat softened bottom portion of the wall against a suitably shaped mandrel, in which case the outer face of the wall will be recessed as shown at 418, or may be moulded in which case the outer recess may not be present. In either case, there will be no projection, or at least no significant projection, of the outer face of the moulded or rolled portion of the wall outside the circumference of the remainder of the wall. The tapered bottom entry assists in insertion of the piston 410, and subsequent insertion of the retainer ring 420 described below.

The retainer ring 420 is moulded from synthetic plastic material and provided with a radially extending flange 422, and has a tapered upper portion 424 having a maximum diameter approximately equal to the internal diameter of the body 402 above the shelf 414, but greater than the internal diameter of the shelf, and a minimum diameter such that it can readily start to enter the tapered bottom entry to the body. A lower portion 426 of the ring above the flange 422 has a smaller external diameter and a height at least equal to the height of portion 416 so that the ring may be pressed into the tapered entry until a shoulder 428 between the upper and lower potions snaps over the shelf 414, thus positively retaining the ring. Preferably the lower portion 426 has an internal profile and height such as to provide snug accommodation of the portion 416 with due allowance for manufacturing tolerances. A small recess 430 may be formed in the inside wall of the body adjacent the shelf 414 to provide additional clearance for the shoulder 428.

The flange 422 is of limited radial extent so that it does not extend beyond the external diameter of the vial body, so that the retainer ring 420 may be inserted prior to filling and capping, but in this case it cannot also provide a finger flange. This problem can be overcome if a flange is required by providing a separately moulded flange 432, with an annular forwardly projecting locking ring 434 which can be snapped into annular groove 436 formed within the ring 420 prior to use of the vial.

I claim:

1. A pharmaceutical vial used for forming a barrel and a piston of a syringe after being filled and capped, comprising a cylindrical glass vial body having at one end an integral open neck and a peripheral external flange around an outer end of the neck, a peripheral rounded edge defining an inner periphery of an open opposite end, and a piston of resilient material having a cylindrical head within and concentric with the cylindrical glass body, the piston maintaining a slidable hermetically sealing relationship with a main inner cylindrical surface of the body, and being located to define a chamber of volume equal to the nominal capacity of the vial between the piston head and the neck of the vial, the piston having integral coupling structure wholly within the body for subsequent connection to a syringe plunger, and the vial being stable when standing on the open end of the body such that it can be conveyed while so standing through vial filling and capping machinery without tipping over, the body being formed adjacent said open end with peripheral radially extending positive retention means for engagement with complementary configurations of a tubular piston retaining member subsequently inserted within said open end of the body to resist overpressure within the body, wherein the retention means is formed by shaping a lower end portion of the body to have a reduced internal diameter such that the retention means is formed by an upwardly facing shoulder at the top of the lower end portion which projects inwardly of the projected circumference of said main interior cylindrical surface, and the lower end portion is located essentially within the projected circumference of a main cylindrical external surface of the body such as to leave the external surface of the body free of projections having an adverse effect on the stability of the vial;

said vial further including a pharmaceutically project within the chamber, a needle penetrable stopper inserted in the neck, and an annular cap crimped over said stopper and the flange of the neck to retain the stopper in hermetic engagement with the neck, the cap being provided with a concentric tubular outward extension for receiving one of a double ended hollow needle and an adaptor for receiving a single ended hollow needle such that one end of the double ended needle, or a hollow needle provided on the adaptor, can penetrate the stopper, and including a finger grip and piston retainer member, wherein the piston retainer member includes a tubular member which is a press fit within the open end of the body of the vial, and a flange at an outer end of the tubular member providing outwardly extending finger tabs, the tubular member being recessed in its external surface adjacent the flange in the vicinity of the finger tabs so as to receive the retention means inward of the interior wall of the body.

2. A vial according to claim 1, wherein a generally cylindrical bottom portion of the body is of reduced internal and external diameter such as to provide a peripheral shoulder between said main internal cylindrical surface and an internal cylindrical surface of said bottom portion, and an outer cylindrical surface of said bottom portion has an external periphery which is essentially within the projected circumference of a main cylindrical external surface of the body, said shoulder forming said retention means, and the reduced internal diameter of the bottom portion being insufficient to prevent insertion of the piston therethrough.

3. A bottomless pharmaceutical vial for incorporation into a syringe, comprising a generally upright cylindrical hollow body with a narrower neck at its top end, a side wall of the body being formed with a bottom edge surrounding a flared bottom opening, with an inner surface of a lower portion of the side wall of the body adjacent said bottom opening extending upwardly to an outward jog in said inner surface, the jog forming an upwardly facing annular shoulder, and the lower portion of the side wall being substantially wholly within a downward projection of an outer surface of the remainder of the side wall, a piston within the body, and a piston retainer ring inserted into the bottom opening of the body beneath the piston, the piston retainer ring having an outer surface with an upper portion tapered to enter the flare of the inner wall of the body adjacent said bottom opening, a lower portion of reduced external diameter, and a downwardly facing shoulder connecting said upper and lower outer face portions, such that the ring may be pressed into said bottom opening until the shoulder snaps over the shelf to retain the ring.

4. A vial according to claim 3, wherein the retainer ring is wholly inward of the downward projection of the outer surface of the side wall.

5. A vial according to claim 4, wherein the retainer ring includes a flange extending beneath the bottom edge of the body but having a diameter no greater than that of the body.

6. A vial according to claim 5, wherein the flange has an internal peripheral groove, and including a separately formed finger flange with a locking ring for subsequent engagement with the groove.

7. A vial according to claim 4, including a separately formed finger flange for connection to the retainer ring following filling and capping of the vial.

8. Syringe kit, comprising:
(i) a first subassembly comprising:
 (a) a glass pharmaceutical vial having an external configuration which is that of a glass serum vial and handleable by filling and caping machinery designed for filling and capping serum vials, but with a circular bottom opening in a horizontal plane defined by a bottom edge if a cylindrical side wall of the vial, any external projection at said bottom edge of the said wall being insufficient to prejudice the stability of the vial when conveyed free-standing through such filling and capping machinery;

(b) a piston including means for subsequent coupling of said piston to a plunger, the piston being formed of resilient material and having sufficient solidity in the absence of the plunger to ensure an hermetic seal with said vial side wall, the piston, including said coupling means, being received wholly within said vial;

(c) a pharmaceutical filled within said vial above said piston through an open neck thereof by a vial filling machine; and (d) a closure applied to the open neck at the top of the vial and retained thereon by an annular cap, the cap and closure being applied by vial capping machinery;

(ii) means applicable to said annular cap and axially displaceable on use of the syringe to project a cannula through said closure into said vial and thus place said vial in communication with means for injecting its contents;

(iii) a plunger engageable with said coupling means to enable the piston to be projected towards said neck within said side wall to expel said pharmaceutical through said injection means; and wherein a shoulder is formed within said bottom edge of the cylindrical side wall, and further including a piston retainer ring engageable with the shoulder within the vial.

9. A kit according to claim 8, further including means for providing a finger grip on said first subassembly and engaging said vial to facilitate operation of said plunger.

10. A kit according to claim 8, wherein the axially displaceable means applicable to the annular cap and the plunger form parts of a second subassembly including said annular cap and the plunger.

11. In a method of producing a prefilled syringe for administering a pharmaceutical preparation, said syringe comprising a generally cylindrical syringe body having a neck at one end and a side wall having a bead finish at the other end, at least a component of the preparation filled into said body, an elastomeric closure closing the body at the neck end and secured by a cap, and an elastomeric piston at said other end forming a hermetic seal with an inside surface of said side wall, needle means for movement relative to the cap to penetrate the elastomeric closure, and plunger means for connection to an outer side of the piston, the improvement wherein:

the syringe is produced by associating components, including said plunger and said needle, with a prefilled vial produced by:

forming said body with height to diameter ratio such that the body is stable, and so that any outward extent of the bead is insufficient to result in interference such as would cause tipping, when the body is conveyed standing on said other end through equipment for filling and capping pharmaceutical vials;

inserting said elastomeric piston wholly within said other end of the body to form a vial open at the neck; and filling said vial through said neck with said pharmaceutical preparation component, and then applying said elastomeric closure on said cap, whilst conveying the vial standing on said other end through equipment for filling and capping pharmaceutical vials.

12. A method according to claim 11, wherein the association of other components includes engaging a piston retainer within said other end of the vial after filling and capping, and wherein the vial with the piston retainer applied is heat sterilized.

13. A method according to claim 11, wherein the step of forming said body so that any outward extent of the bead is insufficient to result in interference such as would cause tipping includes forming the bead to provide an upwardly facing shoulder projecting inwardly of the wall of the body.

14. A method according to claim 11, wherein the step of forming said body so that any outward extent of the bead is insufficient to result in interference such as would cause tipping includes slightly reducing the diameter of a bottom portion of the body, and flaring the open end of said reduced diameter portion of the body to form said bead.

\* \* \* \* \*